US010342450B2

(12) United States Patent
Kortelainen et al.

(10) Patent No.: US 10,342,450 B2
(45) Date of Patent: Jul. 9, 2019

(54) APPARATUS AND METHOD FOR ELECTROENCEPHALOGRAPHIC MEASUREMENT (71) Applicant: CERENION OY, Oulu (FI)

(72) Inventors: Jukka Kortelainen, Oulu (FI); Eero Väyrynen, Oulu (FI); Ilkka Juuso, Oulu (FI)

(73) Assignee: CERENION OY, Oulu (FI)

( * ) Notice: Subject to any disclaimer, the term of this patent is extended or adjusted under 35 U.S.C. 154(b) by 279 days.

(21) Appl. No.: 15/151,873

(22) Filed: May 11, 2016

(65) Prior Publication Data
US 2017/0325702 A1 Nov. 16, 2017

(51) Int. Cl.
A61B 5/0484 (2006.01)
A61B 5/04 (2006.01)
(Continued)

(52) U.S. Cl.
CPC ........ A61B 5/0484 (2013.01); A61B 5/04012 (2013.01); A61B 5/4821 (2013.01); A61M 5/172 (2013.01); A61M 15/00 (2013.01); A61M 19/00 (2013.01); A61N 1/36025 (2013.01); A61N 1/36082 (2013.01); A61N 2/006 (2013.01); A61N 5/0618 (2013.01); A61N 5/0622 (2013.01); A61N 7/00 (2013.01); A61M 5/1723 (2013.01); A61M 2205/52 (2013.01);
(Continued)

(58) Field of Classification Search
None
See application file for complete search history.

(56) References Cited

U.S. PATENT DOCUMENTS 5,315,505 A * 5/1994 Pratt ................. A01K 5/02
600/300
5,699,808 A * 12/1997 John ................. A61B 5/0484
600/483
(Continued)

FOREIGN PATENT DOCUMENTS

WO 2004/100766 A2 11/2004
WO 2011/057028 A1 5/2011
WO 2014/152110 A1 9/2014

OTHER PUBLICATIONS

Massimini, Marcello, et al. "Triggering sleep slow waves by transcranial magnetic stimulation." Proceedings of the National Academy of Sciences 104.20 (2007): 8496-8501.*
(Continued)

Primary Examiner — Patricia Mallari
Assistant Examiner — Jairo H Portillo
(74) Attorney, Agent, or Firm — Oliff PLC (57) ABSTRACT An apparatus comprises a data processing unit and a stimulator. The data processing unit receives first electroencephalographic data based on a measurement of a brain of a person exposed to one or more estimated or measured non-zero amounts of anesthetic drug substance. The data processing unit performs a first comparison between the first electroencephalographic data and corresponding data of a reference brain function, and outputs information about the first comparison. The stimulator provides the brain of the person exposed to the anesthetic drug substance with brain stimulation on the basis of a direct or indirect reception of the information about the first comparison.

15 Claims, 4 Drawing Sheets (51) Int. Cl.
| | |
|---|---|
| A61B 5/00 | (2006.01) |
| A61M 15/00 | (2006.01) |
| A61M 19/00 | (2006.01) |
| A61N 1/36 | (2006.01) |
| A61N 2/00 | (2006.01) |
| A61N 5/06 | (2006.01) |
| A61N 7/00 | (2006.01) |
| A61M 5/172 | (2006.01) |
| A61N 5/067 | (2006.01) |

(52) U.S. Cl.
CPC ............ A61M 2210/0693 (2013.01); A61M 2230/005 (2013.01); A61M 2230/10 (2013.01); A61N 2005/063 (2013.01); A61N 2005/067 (2013.01); A61N 2005/0647 (2013.01); A61N 2005/0651 (2013.01); A61N 2007/0026 (2013.01)

(56) References Cited

U.S. PATENT DOCUMENTS

| | | | | |
|---|---|---|---|---|
| 6,975,901 | B2* | 12/2005 | Philip | A61B 5/0484 600/544 |
| 2004/0079372 | A1* | 4/2004 | John | A61B 5/048 128/204.18 |
| 2007/0142874 | A1* | 6/2007 | John | A61N 1/3605 607/45 |
| 2008/0194981 | A1* | 8/2008 | Sarkela | A61B 5/0484 600/544 |
| 2010/0022907 | A1 | 1/2010 | Perez-Velazquez et al. | |
| 2011/0230747 | A1* | 9/2011 | Rogers | A61B 5/05 600/377 |
| 2011/0275927 | A1* | 11/2011 | Wagner | A61N 1/20 600/411 |
| 2015/0066104 | A1 | 3/2015 | Wingeier et al. | |

OTHER PUBLICATIONS

Fan, Jie et al., "Magnetic Field Projector for Deep Brain Stimulation," IEEE Transactions on Magnetics, vol. 51, No. 11, (Nov. 2011).

Lee, Won Hee et al., "Anatomical Variability Predicts Individual Differences in Transcranial Electric Stimulation Motor Threshold," 35th Annual International Conference of the IEEE EMBS, Osaka, Japan, Jul. (2013), pp. 815-818.

Manganotti, Paolo et al., "Effect of High-Frequency Repetitive Transcranial Magnetic Stimulation on Brain Excitability in Severely Brain-Injured Patients in Minimally Conscious or Vegetative State," Brain Stimulation, vol. 6, (2013), pp. 913-921.

Deng, Zhi-De et al., "Effect of Anatomical Variability on Neural Stimulation Strength and Focality in Electroconvulsive Therapy (ECT) and Magnetic Seizure Therapy (MST)," 31st Annual International Conference of the IEEE EMBS, Minneapolis, Minnesota, (Sep. 2009), pp. 682-688.

Sjaaheim, Haldor et al., "A Portable Medical System for the Early Diagnosis and Treatment of Traumatic Brain Injury," 2014 IEEE International Conference on Systems, Man, and Cybernetics, San Diego, California, (Oct. 5-8, 2014), pp. 2529-2534.

U.S. Appl. No. 141674,318, filed Mar. 31, 2015 in the name of Kortelainen at el.

Jul. 10, 2017 Search Report issued in International Patent Application No. PCT/FI2017/050243.

* cited by examiner

APPARATUS AND METHOD FOR ELECTROENCEPHALOGRAPHIC MEASUREMENT

FIELD

The invention relates to an apparatus and a method for electroencephalographic measurement.

BACKGROUND

Assessing function of the brain of a person with a potential injury which may be caused by a cardiac arrest, a stroke, trauma or the like remains a significant medical challenge. Appropriate treatment, therapeutic interventions and even their development as well as recovery of the person depend on a reliable and early detection of a brain dysfunction.

Modern brain imaging techniques enable the assessment the brain function. However, the imaging techniques are laborious and expensive, and an imaging device is fixed to its position and is thus non-movable. A person with brain injury, in turn, is typically a patient of an intensive care unit whose health doesn't allow his/her movement. The combination makes it challenging or impossible to take the person to the brain examination and set him/her in a proper position in the imaging device. Furthermore, the brain imaging at least almost always requires movement of the person to a different room typically outside the intensive care unit. Thus, a need exists to develop the examination of the brain function of a person with a potential brain injury.

BRIEF DESCRIPTION

The present invention seeks to provide an improvement in the measurement. According to an aspect of the present invention, there is provided an apparatus as specified in claim 1.

According to another aspect of the present invention, there is provided an apparatus in claim 12.

According to another aspect of the present invention, there is provided a method in claim 13.

The solutions according to the invention provide several advantages. It is possible to determine and present a deviation from a normal brain function under precipitation of one or more anesthetic drug substance. The persistence of the deviation may also be tested with stimulation. The at least one property of the stimulation may be selected on the basis of the determined deviation. Further, the selected stimulation may be used to modify the brain function towards the normal brain function.

LIST OF DRAWINGS

Example embodiments of the present invention are described below, by way of example only, with reference to the accompanying drawings, in which.

DESCRIPTION OF EMBODIMENTS

The following embodiments are only examples. Although the specification may refer to "an" embodiment in several locations, this does not necessarily mean that each such reference is to the same embodiment(s), or that the feature only applies to a single embodiment. Single features of different embodiments may also be combined to provide other embodiments. Furthermore, words "comprising" and "including" should be understood as not limiting the described embodiments to consist of only those features that have been mentioned and such embodiments may contain also features/structures that have not been specifically mentioned.

It should be noted that while Figures illustrate various embodiments, they are simplified diagrams that only show some structures and/or functional entities. The connections shown in the Figures may refer to logical or physical connections. It is apparent to a person skilled in the art that the described apparatus may also comprise other functions and structures than those described in Figures and text. It should be appreciated that details of some functions, structures, and the signalling used for measurement and/or controlling are irrelevant to the actual invention. Therefore, they need not be discussed in more detail here. The general prior art concept of the apparatus is described in the patent document U.S. Ser. No. 14/674,318.

Slow waves, the frequency of which is at or below 1 Hz ($f<1$ Hz), may be considered an important EEG signatures of non-rapid eye movement (NREM) sleep. Based on the physiological importance of the slow waves and the possibility to test their generation with anesthetics in a controlled manner, it can be hypothesized that this electrophysiological phenomenon is disrupted in an injured brain. The synchronized activity of large neuronal populations as well as the delicate interaction between cortical and sub-cortical areas required in the formation of the waves can be expected to be sensitive to abnormal brain function. For this purpose, this application refers to an experiment carried out with a plurality of comatose patients of an intensive care unit (ICU) after resuscitation from out-of-hospital cardiac arrest.

The experimental protocol was approved by the institutional Ethics Committee of Oulu University Hospital which follows the Declaration of Helsinki guidelines. The patients' closest relatives were asked for an informed written consent to participate. Because of the reduced oxygen supply during the cardiac arrest, the patients potentially had suffered from hypoxic-ischemic brain injury due to which they had received therapeutic hypothermia treatment as a neuroprotective measure before the experiment. These patients generally represent a substantial diagnostic challenge as detecting the potential diffuse brain injury in the early phase of recovery is highly demanding. In the experiment, the patients' ability to generate anesthetic-induced slow waves was tested by exposing them to varying amounts of anesthetic drug substance (propofol) in a controlled manner. To assess the association between the slow waves and brain injury, the patients' neurological recovery was then followed for six months.

Figure 1:
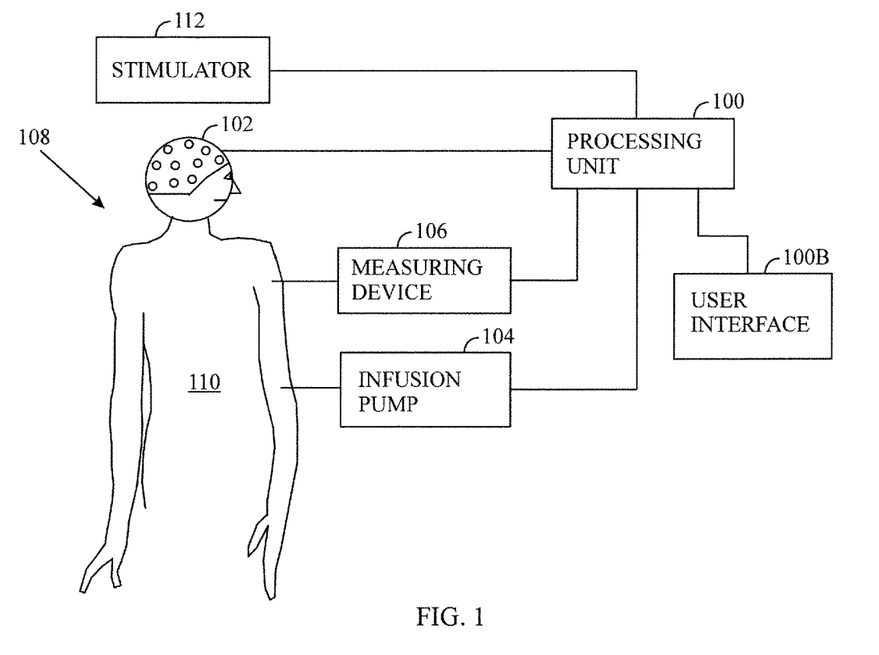
FIG. 1 illustrates an example an apparatus for brain function measurement.

Examine now an example of an apparatus for brain function measurement by means of FIG. 1. The apparatus comprises a data processing unit 100 and a stimulator 112. In an embodiment the apparatus may also comprise electrode system 102, an administration device 104 and/or a blood measuring device 106. The administration device 104 may include or be an infusion pump, for example.

The electrode system 102 is electrically coupled or in contact with the scalp or the brain of a person 108. The electrode system 102 provides the electroencephalographic (EEG) data for the data processing unit 100. The electroencephalographic data may be directly fed from the electrode system 102 to the data processing unit 100 or the electroencephalographic data may first be stored in memory and the electroencephalographic data may later be fed to the data processing unit 100.

Electroencephalography, per se, is a recording of electrical activity of the brain. The electrical activity is measured as a voltage variation caused by the neurons of the brain tissue.

Electroencephalographic data refers to electroencephalographic information which is in an analog or a digital form which can be processed and analyzed in the data processing unit 100. The measured data is processed and analyzed in the data processing unit 100 for determining state(s) of the brain and/or its function. A control action, a decision, result data or a diagnosis may be based on the electroencephalographic data or the determined state(s)/function.

To record EEG signal the system may have a plurality of channels like in the experiment. The number of channels may be 19, without restricting to that. The EEG may be recorded according to the 10/20 international system using an electrode cap with Ag/AgCl electrodes as the electrode system 102. For the recording, Nicolet nEEG Modular Neurodiagnostic System with a v32 Amplifier may be used. The amplifier may have a sampling frequency of 500 Hz and bandwidth of 0.053-500 Hz. A common average reference may be used. For the EEG recording, the patient's sedation is realized with an anesthetic drug substance which may follow the ICU's common practice.

The infusion pump may infuse the anesthetic drug substance, which is in a fluidal form, into the body of the person. The anesthetic drug substance comprises one anesthetic drug or a combination of anesthetic drugs. The anesthetic drug substance may be infused into at least one vein of a circulatory system of the person. The anesthetic drug substance may be infused continuously or may be introduced as one or more boluses. The anesthetic drug substance may then be called an intravenous drug substance. Additionally or alternatively arterial, epidural and/or subcutaneous, intrathecal and muscular infusion may be used. Infusion in this context also includes injection. The infusion pumps can administer anesthetic drug substances very accurately. Manual injections of the anesthetic drug substance are more inaccurate and expensive. Infusion pumps can be used to administer the anesthetic drug substance adaptively such that the input varies with respect to a desired parameter such as time, EEG measurement and the measured concentration of the anesthetic drug substance, for example.

Additionally or alternatively, an inhalation device as the administration device 104 may be used for inhaling the anesthetic drug substance. The inhalation may be continuous or the anesthetic drug substance may be introduced in a step-wise manner, each step increasing or decreasing the dose.

The data processing unit 100 receives first electroencephalographic data based on the EEG measurement of a brain of a person 110 while the person 110 is exposed to one or more estimated or measured non-zero amounts of anesthetic drug substance.

The at least one anesthetic drug substance may have one or more estimated or measured non-zero levels of concentration in the body 108 of the person 110 as a function of time. It is possible to measure the EEG in only one non-zero concentration which may be either estimated or measured. Instead of one level of concentration, the anesthetic drug substance may have a plurality of concentration levels as a function of time. The at least one concentration level may be estimated or measured. The EEG effect of the anesthetic drug substance typically depends on its concentration level in the body 108. The EEG characteristics such as burst suppression pattern may be used for determining the effect or level of the anesthetic drug. The EEG characteristics such as a burst suppression pattern may be used to determine the amount of administration of the anesthetic drug substance. Alternatively or in addition, the EEG characteristic used may include a feature, such as slow wave activity, which is caused by the administration of the drug, and for example the maximal effect of the drug on this feature is utilized. Still alternatively or in addition, the used EEG characteristic may include determination of a change in the feature crossing a predetermined threshold in the range of the slow wave activity, which is caused by the administration of the drug. The predetermined threshold may be based on experience of a person skilled in the art. The predetermined threshold may be based on simulation. The predetermined threshold may be based on the expected effect of the drug, the effect and use being published in the literature. Because the effect of the drug varies as a function of time a person skilled in the art knows when the predetermined threshold is crossed on the basis of his/her knowledge.

In an embodiment, the administration device 104 may adjust an input of the anesthetic drug substance which is introduced into the body 108. The term "input" refers to an infusion rate or dosing of the anesthetic drug substance. In this manner, the concentration or the EEG effect of the anesthetic drug substance in the body 110 at a certain moment may be estimated and controlled on the basis of the adjusted input.

In an embodiment, the adjusting of the input includes adjusting an amount of the anesthetic drug substance per time unit. In an embodiment, the adjusting of the input includes adjusting an amount of the anesthetic drug substance on the basis of EEG characteristics such as burst suppression pattern. The input may depend on a type of the anesthetic drug or combination of anesthetic drugs. In an embodiment, the adjusting of the doses includes the adjusting an administration frequency of the doses of the anesthetic drug substance. The rate of the doses may be varying as a function of time, for example. The introduction of the anesthetic drug substance causes the one or more levels of concentration of the anesthetic drug substance in the body of the person.

The EEG effect of the at least one anesthetic drug substance to the brain function may be estimated on the basis of the input. The EEG effect depends on the concentration of the anesthetic drug substance in the brain or in blood which, in turn, depends on the input. The use of the anesthetic drug substance gives basis for the measurement. The anesthetic drug substance causes unconsciousness to the person 110. Additionally or alternatively, the anesthetic drug substance causes amnesia, analgesia and/or paralysis to the person 110.

The data processing unit 100 performs a first comparison between the first electroencephalographic data and the corresponding data of a normal brain function which may be a reference brain function. In general the first electroencephalographic data may be based on any EEG signal or any part of the EEG signal. The comparison may measure similarity between the first electroencephalographic data and the corresponding data of the normal/reference brain function. The similarity measurement may be based on correlation, for example.

The data processing unit 100 outputs information about the first comparison. The data processing unit 100 may comprise a user interface 100B which may be used to present the information about the comparison visibly or audibly. The visible presentation may include alphanumeric symbols and/or a graphic representation. The user interface 100B may include a screen, a loudspeaker and/or a printer for presenting the information.

The stimulator 112 then provides brain stimulation for the brain of the person 110 exposed to the anesthetic drug substance on the basis of a direct or indirect reception of the information about the first comparison.

In an embodiment, the data processing unit 100 may form first result data which may be based on activity of slow waves of the first electroencephalographic data of the person 110 under the influence of the anesthetic drug substance. In general the first result data may be based on any EEG signal or any part of the EEG signal.

In an embodiment, the at least one anesthetic drug substance may be administered so much that the burst suppression pattern is observed in the EEG measurement. The data processing unit 100 or a nursing staff may make the observation of the burst suppression pattern.

In more details, EEG signal samples lasting a few minutes, such as 5 min, may be extracted at each level of administration of the anesthetic drug substance. The samples may be taken in the end of the 30-min period just before a change in the infusion rate as well as in the end of the experiment corresponding to the collection of the drug concentration blood samples. The period is chosen such that the anesthetic drug substance causes an EEG effect in the person (see also FIG. 9). The period may last from a few minutes to tens of minutes. The EEG signal sequences may have lengths from seconds to tens of seconds. The length may be 30 sec, for example. These signals may be filtered using a low-pass FIR filter (Finite Impulse Response filter) with a cutoff frequency of 48 Hz, for example, before the calculation of a power spectral density (PSD) estimate using Welch's averaged periodogram method, for example. The estimates may be created using a 5 sec Hamming window or the like and 4.9 sec overlap, for example. An average over said plurality of PSD estimates representing the same infusion rate the anesthetic drug substance may then be calculated to improve the robustness of the estimate. From the averaged PSD estimate, the components below or at 1 Hz may be summed to represent low-frequency EEG power. Finally, an average low-frequency power quantifying the patient's slow wave activity at certain infusion rate may be calculated over the all EEG channels. Additionally or alternatively, also other kind of approaches to form one or more variables describing the slow wave activity (<1 Hz) could be used. The slow wave activity may be determined from continuous EEG or bursts occurring during burst suppression pattern. To assess the relative changes in the activity at different infusion rates, the values may be normalized using the individual average powers at the infusion rate 0 mg/kgh of anesthetic drug substance such as propofol. In an embodiment, the slow wave activity may also be presented relative to the EEG activity for example by dividing the power in the low frequencies (<1 Hz) by the total power of EEG. In an embodiment, the slow wave activity may also be presented relative to the EEG activity for example by dividing the power in the low frequencies (<1 Hz) by the power of EEG on one or more specific frequency bands which may or may not include the low frequencies.

The computational EEG analysis may be carried out in the data processing unit 100 with Matlab technical computing language and the topographic plots may be made with EEGLAB, for example.

In an embodiment, the data processing unit 100 may perform detection whether the first result data deviates from the corresponding data of the normal/reference brain function. The data processing unit 100 may compare the first result data and the corresponding data of the normal/reference brain function. If the similarity between the first result data and the corresponding data of the normal/reference brain function is large enough, there is no deviation. If, on the other hand, the similarity between the first result data and the corresponding data of a normal/reference brain function is small, there is a deviation. The measurement of similarity may be based on correlation. For example, the comparison of slow wave activity may be determined on the basis of the power of the signal in low-frequencies (<1 Hz). The large enough similarity of the correlation may be equal to or more than about 50%. The small similarity of the correlation may be less than about 50%. The reference brain function may refer here to a normal function of a healthy brain or to an average of normal functions of healthy brains.

In an embodiment, the data processing unit 100 may output information about the deviation if the first result data deviates from the corresponding data of the normal/reference brain function. The output first comparison comprises the information about the deviation.

In an embodiment, the stimulator 112 may provide brain stimulation for the brain of the person 110 exposed to the anesthetic drug substance on the basis of a direct or indirect reception of the information about the deviation.

The stimulator 112 may thus provide the brain of the person 110 with the brain stimulation in response to the detection of the deviation from the normal/reference brain function.

In an embodiment, the stimulator 112 may receive the information about the comparison, which may comprise the information about the deviation indirectly from a nursing staff through the user interface 100B. The nursing staff may input the information because the user interface 100B presents the information about the deviation output by the data processing unit 100 for the nursing staff.

In an embodiment, the stimulator 112 may receive the information about the comparison, which may comprise the information about the deviation, directly from the data processing unit 100 through an operative connection between the data processing unit 100 and the stimulator 112. The operative connection may be wired or wireless.

In an embodiment, the data processing unit 100 may, for example, detect the deviation associated with a slow wave activity under the measured or estimated influence of the anesthetic drug substance. In an embodiment, the data processing unit 100 may, for example, detect the deviation associated with a lack of the slow wave activity under the measured or estimated influence of the anesthetic drug substance. The deviation can alternatively or in addition be associated with the activity in some other EEG band such as delta (1-4 Hz), theta (4-8 Hz), alpha (8-12 Hz), beta (>12 Hz), or some other specific frequency band or the total power of EEG. The deviation can also be associated with the relative activity in these bands. The deviation can also be associated with the phase coupling of the signal in different topographic areas. The deviation may also be associated with the detection of epileptic activity in the signal.

The deviation may also be associated with the activity in these bands in relation to the topographic areas, that are, the spatial location of the electrodes on the scalp.

In an embodiment, the data processing unit 100 may, for example, detect the deviation associated with slow wave activity below the normal/reference brain function under the measured or estimated influence of the anesthetic drug substance.

In an embodiment, the data processing unit 100 may, for example, detect the deviation associated with slow wave activity above the normal/reference brain function under the measured or estimated influence of the anesthetic drug substance.

In an embodiment, the data processing unit 100 may, for example, detect the deviation associated with a wave activity nonexistent in the normal/reference function of the healthy brain under the exposure to the anesthetic drug substance. That is, the detected deviation may be any abnormal brain function under the exposure to the anesthetic drug substance. The stimulator 112 may then provide the brain of the person 110 exposed to the anesthetic drug substance with brain stimulation on the basis of a direct or indirect reception of the information about the deviation. The EEG samples may be evaluated for abnormalities such as epileptic activity or suppression. Artifacts, in turn, may be removed automatically or by a clinical neurophysiology specialist. Artifacts may come from EOG (ElectroOculoGraphy), EMG (ElectroMyoGraphy) or movement, for example. From each signal sample, a plurality of representative artifact-free sequences of the first result data may be picked for further analysis in the processing unit 100.

Unlike those who recover well, the patients with poor neurological outcome are typically unable to generate substantial anesthetic-drug-substance-induced slow wave activity without stimulation. In addition to slow waves, the anesthetic-induced activity in other EEG bands such as delta (1-4 Hz), theta (4-8 Hz), alpha (8-12 Hz), beta (>12 Hz), or some other specific frequency band or the total power of EEG might differ from the reference or normal in patients with poor neurological outcome. The anesthetic-induced relative activity in these bands may also differ from the reference or normal in patients with poor neurological outcome. The anesthetic-induced activity changes in these bands in relation to the topographic areas may also differ from the reference or normal in patients with poor neurological outcome. The anesthetic-induced phase coupling of the signal in different topographic areas may also differ from the reference or normal in patients with poor neurological outcome. The anesthetic-induced changes in EEG may also reveal abnormal activity such as epileptic activity in patient with poor neurological outcome and not in patients who recover well.

In the case of the slow wave activity, the change in the low-frequency EEG power with respect to the change in concentration of the anesthetic drug substance is thus non-significant. The absolute effect is often most pronounced in the prefrontal and temporal areas in which the slow wave activity should normally be strongest at high anesthetic drug substance infusion rates. However, a clear relative change can be observed in all channels regardless of the brain region. In general, the patients with poor neurological outcome have brain activity deviating from the normal/reference brain activity. Consequently, anesthetic-drug-substance-induced change in the low-frequency power may be considered to have a statistically significant difference between those who recover well and those who have the poor outcome.

When the stimulator 112 provides the brain with the stimulation, the state of the brain activity may change. It may happen that during the stimulation, the slow wave activity returns, the brain activity changes to normal or the brain activity at least changes towards normal in the brain exposed to the one or more estimated or measured non-zero amounts of the anesthetic drug substance. It may also happen that because of the stimulation, the slow wave activity is permanently changed so that the brain activity is normal or the brain activity has at least changed towards normal.

In an embodiment, the stimulator 112 may expose the brain to magnetic, electric, mechanic, chemical or thermal influence, or the like. The magnetic and/or electric influence may be radiational, for example. The electric influence may be transferred as electromagnetic radiation or through galvanic contact. The mechanical influence may be acoustic, for example, which is also radiational.

Figure 2:
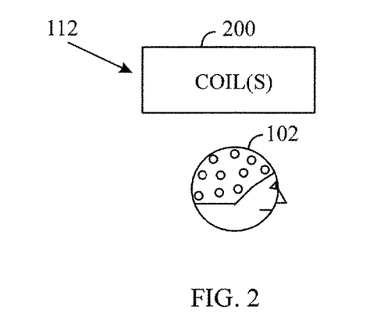
FIG. 2 illustrates an example of a magnetic stimulator.

In an embodiment an example of which is illustrated in FIG. 2, the stimulator 112 may comprise at least one a coil 200 for providing the brain with magnetic stimulation. The stimulation may be performed transcranially so that the coil or the coils are placed outside the head in the proximity of the area stimulated. When alternating electric current is fed to the coil 200, an alternating magnetic field is generated. The stimulation may be performed in a repeated manner so that magnetic stimulation pulses are given repeatedly in a specific frequency. The frequency may be for example approximately 0.8 Hz or 5 Hz and the stimulation may be continued for example for about 30 minutes. The stimulation may be given to a specific location on the scalp such as the area over the sensorimotor cortex to stimulate a specific area of the cortex. The stimulation intensity may be for example 65-85% of maximal stimulator output corresponding to maximal electric field of 150-180 V/m.

Figure 3:
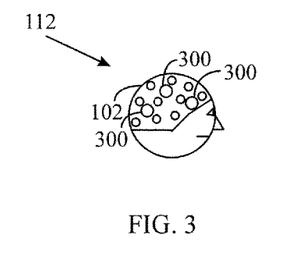
FIG. 3 illustrates an example of an electric stimulator.

In an embodiment an example of which is illustrated in FIG. 3, the stimulator 112 may comprise at least one stimulating electrode 300 for providing the brain with electric stimulation. The at least one stimulating electrode 300 may be included in the electrode system 102 or separate from the electrode system 102. The electrode 300 may transmit electromagnetic radiation wirelessly or feed alternating or direct electric current to the brain through the galvanic contact with the brain. The stimulation may be performed transcranially so that the electrode or the electrodes are placed on the scalp in the proximity of the area stimulated. The stimulation may be given in an oscillatory manner so that the amplitude of the direct current of the direction of the alternating current is changed in a specific frequency. The frequency may be for example approximately 0.8 Hz or 5 Hz and the stimulation may be continued for example for about 30 minutes. The stimulation may be given to a specific location on the scalp such as the area over the frontal cortex to stimulate a specific area of the cortex. With direct current stimulation, the anodal electrode (the electrode with positive polarity) may be located over the frontal cortex and the cathodal electrode (the electrode with negative polarity) may serve as a reference electrode and may be placed on the deltoid muscle. The stimulation current may vary for example between 0 and 0.6 mA and the maximum current density could be approximately 0.5 $mAcm^{-2}$.

Alternatively or in addition to the stimulation on the scalp, the electrical stimulation may be applied directly to the brain tissue by placing the electrodes on the surface of the cortex or inside the brain tissue in which case the approach is called deep brain stimulation.

Figure 4:
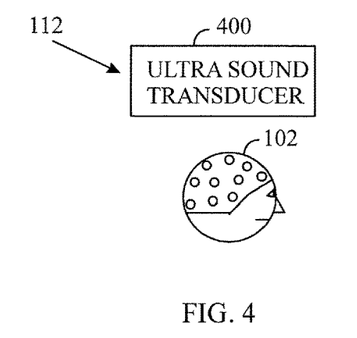
FIG. 4 illustrates an example of an ultrasound stimulator.

In an embodiment an example of which is illustrated in FIG. 4, the stimulator 112 may comprise at least one an ultrasound transducer 400 for providing the brain with acoustic stimulation. The ultrasound transducer 400 may direct ultrasound to the whole brain or a section of the brain.

In an embodiment an example of which is similar to those illustrated in FIGS. 2 to 4, the stimulator 112 may comprise at least one optical fiber or at least one source of optical radiation for providing the brain with optical stimulation. The source of optical radiation may comprise at least one LED (Light Emitting Diode) or at least one laser, for example. The at least one optical fiber or the at least one source of optical radiation may direct the optical stimulation to the whole brain, a section of the brain or several sections of the brain. In optical stimulation, an optogenetic approach may be combined. In this approach, the neurons have been made sensitive to optical stimulation by genetic modification.

Figure 5:
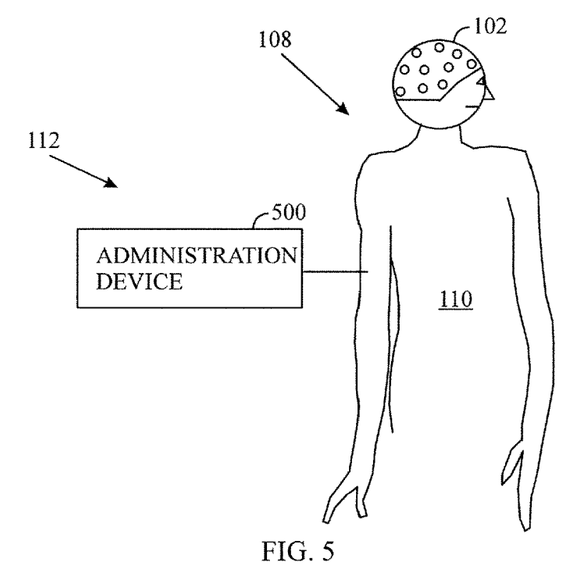
FIG. 5 illustrates an example of an administration device for chemical stimulation.

In an embodiment an example of which is illustrated in FIG. 5, the stimulator 112 may comprise at least one stimulating administration device 500 for providing the brain with chemical stimulation. The stimulating administration device 500 may comprise an infusion pump and/or an inhalation device similar to the administration device 104. The stimulating administration device 500 may provide the person 110 with at least one stimulating drug. A stimulating drug here means a drug which may induce a missing activity or reduce an abnormal activity. For example, the stimulating drugs for slow wave activity could be intravenous GABAergic anesthetics, inhalational GABAergic anesthetics, opioids and/or alpha2-adrenergic anesthetics. The group of the other intravenous GABAergic anesthetics may include etomidate, thiopental, and/or methohexital, for example. The group of the inhalational GABAergic anesthetics may include isoflurane, desflurane, and/or sevoflurane, for example. The group of the opioids may include morphine, fentanyl, alfentanil, remifentanil, and/or sufentanil, for example. The group of the alpha2-adrenergic anesthetics may include dexmedetomidine or the like, for example.

In an embodiment, the data processing unit 100 may determine a stimulation property of the stimulator 112 from at least two properties on the basis of the first comparison. In an embodiment, the data processing unit 100 may determine a stimulation property of the stimulator 112 from at least two properties on the basis of the detected deviation from the normal/reference brain function.

In an embodiment, the data processing unit 100 may determine at least one property of the stimulator 112 of the following: type, strength, frequency, and duration of the stimulation performed by the stimulator 112. For example, a stimulation treatment with transcranial magnetic or electric stimulation may be applied with a frequency of approximately 0.8 Hz for about 30 minutes if the lack of the slow wave activity of about 50% or more is detected. In the case of chemical stimulation, the strength may mean an amount or a dose of the stimulating drug or the duration of the treatment with the stimulating drug. The frequency may refer to a frequency of a stimulating acoustic, electric or magnetic signal, or a repetition rate of the stimulation.

In an embodiment related to the type, the data processing unit 100 may determine whether to use the at least one stimulating coil 200, the at least one stimulating electrode 300, the at least one ultrasound transducer 400, the at least one administration device 500 or any combination thereof.

Further, the data processing unit 100 may perform a second comparison between the second electroencephalographic data and at least one of the following: the data of the normal/reference brain function, and the first result data. This comparison with respect to the normal/reference brain function may be performed in a manner similar to that associated with the first electroencephalographic data. The comparison with respect to the first electroencephalographic data may also be performed in a comparison manner similar to the comparison associated with the normal/reference brain function. Finally, the data processing unit 100 may present the information about the second comparison.

In an embodiment, the data processing unit 100 may receive second electroencephalographic data based on a measurement of the brain of the person 110 under exposure of both the one or more estimated or measured non-zero amounts of the anesthetic drug substance and the stimulation performed by the stimulator 112. Then the data processing unit 100 may form a second result data based on the EEG of the second electroencephalographic data which refers to brain activity. In an embodiment, the data processing unit 100 may form a second result data based on activity of the slow waves or other brain activity of the second electroencephalographic data.

Further, the data processing unit 100 may determine whether the second result data deviates from at least one of the following: the data of the normal/reference brain function, and the first result data. This determination with respect to the normal/reference brain function may be performed in a manner similar to that associated with the first detection. The determination with respect to the first result data may also be performed in a comparison manner similar to the comparison associated with the normal/reference brain function. Finally, the data processing unit 100 may present the second detection. The second detection may be presented using a screen, a display, or the second detection may be printed.

In an embodiment, the data processing unit 100 may predict a neurological function level of the person 110 on the basis of the second detection, and present the prediction.

In an embodiment, the data processing unit 100 may predict a further development towards a normal neurological activity function of the person 110 if the activity of the slow waves of the second result data is closer to the normal brain activity than that of the first result data.

In an embodiment, the data processing unit 100 may predict a further development towards a normal/reference neurological activity function of the person 110 if the second electroencephalographic data is closer to the normal/reference brain activity than that of the first electroencephalographic data.

In an embodiment, the data processing unit 100 may predict a further development towards a poor state from the normal neurological activity function if the activity of the slow waves of the second result data is farther from the normal/reference brain activity than that of the first result data.

In an embodiment, the data processing unit 100 may predict a further development towards a poor state from the normal neurological activity function if the activity of the slow waves of the second electroencephalographic data is farther from the normal/reference brain activity than that of the first electroencephalographic data.

In an embodiment, the first and second result data may be indices or variables derived from the slow wave activity. The second result data may be used to predict a good neurological recovery of the person or a poor neurological recovery of the person. The good neurological recovery of the person may be possible if the activity of the slow waves in the second result data is higher than a predetermined threshold. The predetermined threshold may be decided on the basis of experience. In an embodiment, the predetermined threshold may be at a level where the activity increases more than a certain percentage after any rate of administration of the anaesthetic drug substance. In an embodiment, the predetermined threshold may be at a level where the activity increases more than 50%, for example, after any rate of administration of the anaesthetic drug substance. The data processing unit 100 may, in a similar manner, form and output the second result data which may be used to predict severe disability, coma or death if the activity of the slow waves is lower than a predetermined threshold. However, the second result data, per se, doesn't predict the good or poor outcome but requires a professional's decision of the condition of the person 110.

In an embodiment, the good neurological recovery of the person may be predicted if the activity of the slow waves in the second result data is higher than in the first result data.

Figure 6:
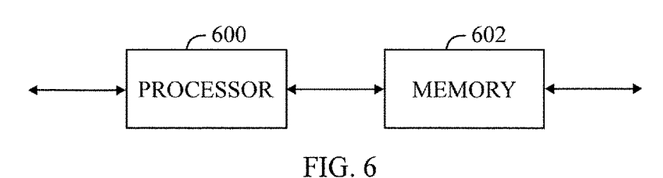
FIG. 6 illustrates an example of a data processing unit.

In an embodiment an example of which is illustrated in FIG. 6, the data processing unit 100 may comprise a computer comprising at least one processor 600 and at least one memory 602. Their operation is based on a sequence of program commands of the computer program controlling the operation, stored in the memory. The one or more memories 602 with the one or more processors 600 and the computer program with the one or more processors 600 may cause the apparatus to control the following. The data processing unit 100 may be controlled to receive first electroencephalographic data based on a measurement of a brain of a person 110 exposed to one or more estimated or measured non-zero amounts of anesthetic drug substance. The data processing unit 100 may be controlled to perform a first comparison between the first electroencephalographic data and corresponding data of a normal/reference brain function. The data processing unit 100 may be controlled to output information about the first comparison. The stimulator 112 may be controlled to provide the brain of the person 110 exposed to the anesthetic drug substance with brain stimulation on the basis of a direct or indirect reception of the information about the first comparison.

Instead of or in addition to using the at least one processor 600 and the at least one memory 602, controlling may be implemented as one or more integrated circuits, such as an application-specific integrated circuit ASIC. Other equipment embodiments are also feasible, such as a circuit constructed of separate logic devices. A hybrid of these different implementations is also possible. The computational EEG analysis may be carried out with Matlab technical computing language and the topographic plots may be made with EEGLAB, for example.

In an embodiment, the anesthetic drug may be propofol. In addition to or instead of propofol the anesthetic drug substance may be other anesthetics known to affect slow wave activity. In an embodiment, and more generally, the at least one anesthetic drug substance may be selected from the following groups of other intravenous GABAergic anesthetics, inhalational GABAergic anesthetics, opioids and alpha2-adrenergic anesthetics.

The group of the other intravenous GABAergic anesthetics may include etomidate, thiopental, and/or methohexital, for example.

The group of the inhalational GABAergic anesthetics may include isoflurane, desflurane, and/or sevoflurane, for example.

The group of the opioids may include morphine, fentanyl, alfentanil, remifentanil, and/or sufentanil, for example.

The group of the alpha2-adrenergic anesthetics may include dexmedetomidine or the like, for example.

Figure 7:
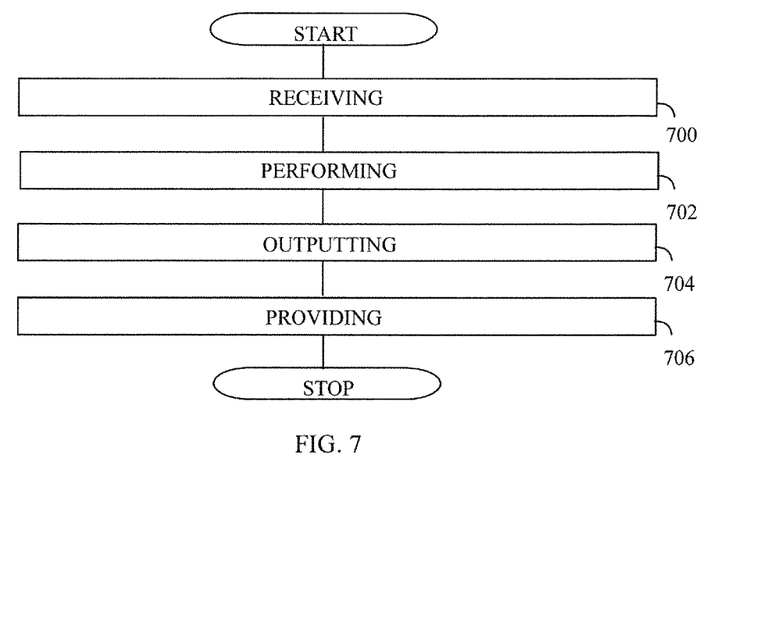
FIG. 7 illustrates an example of a flow chart of a measuring method.

FIG. 7 is a flow chart of the measurement method. In step 700, first electroencephalographic data based on a measurement of a brain of a person 110 exposed to one or more estimated or measured non-zero amounts of anesthetic drug substance are received by a data processing unit 100. In step 702, a first comparison between the first electroencephalographic data and corresponding data of a normal/reference brain function is performed by the data processing unit 100. In step 704, information about the first comparison is output by the data processing unit 100. In step 706, the brain of the person 110 exposed to the anesthetic drug substance is provided with stimulation on the basis of a direct or indirect reception of the information about the comparison.

The method shown in FIG. 7 may be implemented as a logic circuit solution or computer program. The computer program may be placed on a computer program distribution means for the distribution thereof. The computer program distribution means is readable by a data processing device, and it encodes the computer program commands, carries out the measurements and optionally controls the processes on the basis of the measurements.

The computer program may be distributed using a distribution medium which may be any medium readable by the controller. The medium may be a program storage medium, a memory, a software distribution package, or a compressed software package. In some cases, the distribution may be performed using at least one of the following: a near field communication signal, a short distance signal, and a telecommunications signal.

The distribution medium, in turn, may be a readable medium, a readable program storage medium, a readable memory, a readable software distribution package, or a readable compressed software package.

Figure 8:
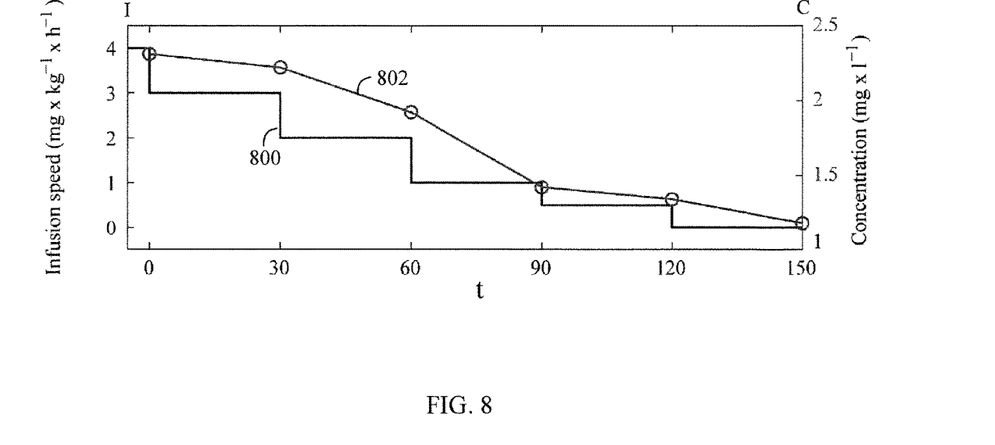
FIG. 8 illustrates examples a curve of input of the anesthetic drug substance with an infusion pump and a curve of concentration of the anesthetic drug substance in blood of a person with good outcome.

FIG. 8 illustrates examples a curve 800 of input of the anesthetic drug substance with an infusion pump and a curve 802 of concentration of the anesthetic drug substance in blood of a person with good outcome. The good outcome refers to a further development towards a normal neurological function. The first vertical axis denotes input I defined by the mass unit (mg) of the anesthetic drug substance per both time unit (h) and the mass unit (kg) of the person to whom the anesthetic drug substance is administered. The second vertical axis denotes the concentration C (mg/l) of the anesthetic drug substance in blood. The horizontal axis denotes time T in minutes. In this experiment only one anesthetic drug was used, and the anesthetic drug was propofol. The amount of administered propofol was decreased step-wise from 4 mg/kgh to 0 mg/kgh in every 30 min. The dosing of the anesthetic drug substance may decrease in every step the same amount. The dosing of propofol may decrease in every step the same amount, for example about 1 mg/kgh. The dosing of propofol decreased first 1 mg/kgh and then 0.5 mg/kgh in the example of FIG. 8. The concentration of propofol in blood was measured just before the next decrease of the infusion rate and in the end of the experiment. The highest concentration of propofol 2.39±0.45 mg/l (mean±std) was achieved with the highest infusion rate 4 mg/kgh and the lowest concentration of propofol 0.98±0.26 mg/l was achieved with the lowest infusion rate 0 mg/kgh. The concentration values between groups, i.e. the patients with good and poor neurological outcome, were comparable. The poor outcome refers to a poor or no change towards the normal neurological function. That is, the neurological function regresses, remains the same or the potential progress in the neurological function is so slight that it will result in a severe disability, coma or death. Thus, even the potential progress in the neurological function associated with the poor outcome cannot be considered development.

In an embodiment, the amount of the anesthetic drug substance may instead of decreasing be increased from 0 mg/kgh to a desired maximum level. The dosing may be continuous or discrete i.e. stepwise. In an embodiment, the starting level of the anesthetic drug substance may be at 0 mg/kgh or at some other level, and the amount of the anesthetic drug substance may be increasingly administered until a level of the burst suppression pattern is reached. The burst suppression pattern is detectable in the EEG signal.

Figure 9:
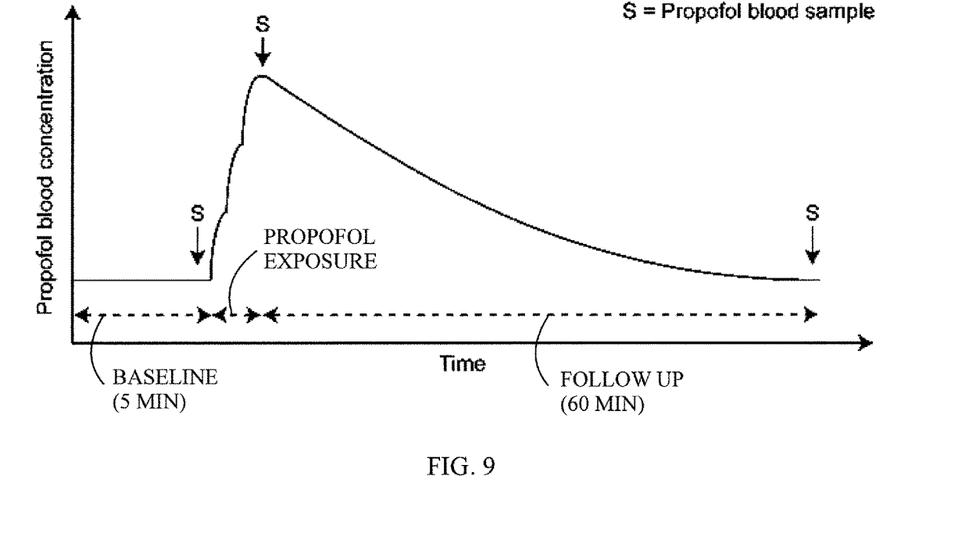
FIG. 9 illustrates an example of a clinical protocol during which the stimulation is applied.

FIG. 9 illustrates an example of the clinical protocol during which the stimulation may be applied. During this protocol an EEG signal is recorded. At first, a baseline recording may be made for example for 5 minutes during which there is no administration of the drug or the administration is kept fixed. After this, the administration of the drug is increased for example by increasing the infusion rate or with one or more drug boluses. After reaching the required drug effect for example determined from the EEG on the basis the burst suppression pattern or the like. Alternatively or in addition, the EEG characteristic used may include a feature, such as slow wave activity, which is caused by the administration of the drug, and for example, the maximal effect of the drug on this feature is utilized. Still alternatively or in addition, the used EEG characteristic may include determination of a change in the feature crossing a predetermined threshold in the range of the slow wave activity, which is caused by the administration of the drug. The predetermined threshold may be based on experience of a person skilled in the art. The predetermined threshold may be based on simulation. The predetermined threshold may be based on the expected effect of the drug, the effect and use being published in the literature. Because the effect of the drug varies as a function of time a person skilled in the art knows when the predetermined threshold is crossed on the basis of his/her knowledge.

The administration of the drug may be reduced for example to zero or back to a fixed rate that was used before increasing the administration. During this protocol, deviations from normal/reference EEG behavior are detected and the stimulation is applied based on these deviations. This deviation could, for example, be the lack of EEG slow wave activity. The stimulation could, for example, take place after reducing the administration of drug and the EEG changes from burst suppression pattern back to continuous. The duration of the stimulation could be about 30 minutes, for example.

It will be obvious to a person skilled in the art that, as technology advances, the inventive concept can be implemented in various ways. The invention and its embodiments are not limited to the example embodiments described above but may vary within the scope of the claims.

The invention claimed is:

1. An apparatus comprising:
one or more processors; and
a stimulator, wherein the one or more processors are configured to:
receive first electroencephalographic data based on a measurement of a brain of a person exposed to one or more non-zero amounts of an anesthetic drug substance;
perform a first comparison between the first electroencephalographic data and corresponding data of a reference brain function, the reference brain function being a normal function of a healthy brain or an average of normal functions of healthy brains;
based on a result of the first comparison, determine whether the first electroencephalographic data deviates from the corresponding data of the reference brain function, a deviation referring to an abnormal brain function; and
in response to determining that the first electroencephalographic data deviates from the corresponding data of the reference brain function perform one of:
(A) directly cause the stimulator to provide the brain of the person exposed to the one or more non-zero amounts of the anesthetic drug substance with brain stimulation on the basis of information about the deviation from the corresponding data of the reference brain function, the brain stimulation being provided to cause brain activity of the brain to change in a direction toward the normal function of the healthy brain or the average of normal functions of healthy brains; and
(B) output, to a user, the information about the deviation from the corresponding data of the reference brain function, receive, from the user, indirect information about the deviation from the corresponding data of the reference brain function, and cause the stimulator to provide the brain of the person exposed to the anesthetic drug substance with brain stimulation on the basis of the indirect information about the deviation from the corresponding data of the reference brain function, the brain stimulation being provided to cause brain activity of the brain to change in a direction toward the normal function of the healthy brain or the average of normal functions of healthy brains.

2. The apparatus of claim 1, wherein the first electroencephalographic data is data including an activity of slow waves.

3. The apparatus of claim 1, wherein the indirect information about the deviation is received from a user interface.

4. The apparatus of claim 2, wherein
the reference brain function is a normal brain function of a healthy brain under the exposure to the one or more non-zero amounts of the anesthetic drug substance, and
the one or more processors are further configured to:
determine whether the first electroencephalographic data deviates from the corresponding data of the reference brain function based on at least one of: a lack of slow wave activity, slow wave activity below the reference brain function, slow wave activity above the reference brain function, and a wave activity nonexistent in the reference brain function.

5. The apparatus of claim 1, wherein the stimulator comprises at least one of the following: a coil for providing the brain with magnetic stimulation, an electrode for providing the brain with electric stimulation, an ultrasound transducer for providing the brain with acoustic stimulation, a device for providing the brain with optical stimulation, and an administration device for providing the brain with chemical stimulation.

6. The apparatus of claim 1, wherein the one or more processors are configured to determine a stimulation property of the stimulator on the basis of the first comparison.

7. The apparatus of claim 1, wherein the one or more processors are configured to determine at least one of: a type, a strength, a frequency, and a duration of the brain stimulation performed by the stimulator.

8. The apparatus of claim 1, wherein the one or more processors are configured to:
receive second electroencephalographic data based on a measurement of the brain of the person under exposure of both the one or more non-zero amounts of the anesthetic drug substance and the brain stimulation performed by the stimulator;
perform a second comparison between the second electroencephalographic data and at least one of the following: the corresponding data of the reference brain function, and the first electroencephalographic data; and
present information about the second comparison.

9. The apparatus of claim 8, wherein the second electroencephalographic data includes an activity of slow waves.

10. The apparatus of claim 8, wherein the one or more processors are further configured to predict a neurological function level of the person on the basis of the second comparison, and present the prediction.

11. The apparatus of claim 10, wherein the one or more processors are further configured to predict, as the prediction, a further development towards at least one of the following: a reference neurological activity function of the person if the second electroencephalographic data is closer to brain activity of the reference brain function than brain activity of the first electroencephalographic data, and a poor development from the reference neurological activity function if the second electroencephalographic data is farther from the brain activity of the reference brain function than the brain activity of the first electroencephalographic data.

12. The apparatus of claim 1, wherein the apparatus is an apparatus for evaluating an abnormality in brain function.

13. The apparatus of claim 1, wherein the abnormal brain function includes epileptic activity.

14. An apparatus comprising:
a stimulator;
one or more processors; and
one or more memories including computer program code, wherein the computer program code, when executed by the one or more processors, causes the one or more processors to:
receive first electroencephalographic data based on a measurement of a brain of a person exposed to one or more non-zero amounts of an anesthetic drug substance;
perform a first comparison between the first electroencephalographic data and corresponding data of a reference brain function, the reference brain function being a normal function of a healthy brain or an average of normal functions of health brains;
based on a result of the first comparison, determine whether the first electroencephalographic data deviates from the corresponding data of the reference brain function, a deviation referring to an abnormal brain function; and
in response to determining that the first electroencephalographic data deviates from the corresponding data of the reference brain function perform one of:
(A) directly cause the stimulator to provide the brain of the person exposed to the one or more non-zero amounts of the anesthetic drug substance with brain stimulation on the basis of information about the deviation from the corresponding data of the reference brain function, the brain stimulation being provided to cause brain activity of the brain to change in a direction toward the normal function of the healthy brain or the average of normal functions of healthy brains; and
(B) output, to a user, the information about the deviation from the corresponding data of the reference brain function, receive, from the user, indirect information about the deviation from the corresponding data of the reference brain function, and cause the stimulator to provide the brain of the person exposed to the anesthetic drug substance with brain stimulation on the basis of the indirect information about the deviation from the corresponding data of the reference brain function, the brain stimulation being provided to cause brain activity of the brain to change in a direction toward the normal function of the healthy brain or the average of normal functions of healthy brains.

15. A method comprising:
receiving, by one or more processors, first electroencephalographic data based on a measurement of a brain of a person exposed to one or more non-zero amounts of an anesthetic drug substance;
performing, by the one or more processors, a first comparison between the first electroencephalographic data and corresponding data of a reference brain function, the reference brain function being a normal function of a healthy brain or an average of normal functions of healthy brains;
based on a result of the first comparison, determining, by the one or more processors, whether the first electroencephalographic data deviates from the corresponding data of the reference brain function, a deviation referring to an abnormal brain function; and
in response to determining that the first electroencephalographic data deviates from the corresponding data of the reference brain function perform one of:
(A) directly causing, by the one or more processors, a stimulator to provide the brain of the person exposed to the one or more non-zero amounts of the anesthetic drug substance with brain stimulation on the basis of information about the deviation from the corresponding data of the reference brain function, the brain stimulation being provided to cause brain activity of the brain to change in a direction toward the normal function of the healthy brain or the average of normal functions of healthy brains; and
(B) outputting, by the one or more processors, to a user, the information about the deviation from the corresponding data of the reference brain function, receiving, by the one or more processors, from the user, indirect information about the deviation from the corresponding data of the reference brain function, and causing, by the one or more processors, the stimulator to provide the brain of the person exposed to the anesthetic drug substance with brain stimulation on the basis of the indirect information about the deviation from the corresponding data of the reference brain function, the brain stimulation being provided to cause brain activity of the brain to change in a direction toward the normal function of the healthy brain or the average of normal functions of healthy brains.

\* \* \* \* \*